(12) United States Patent
Melsheimer

(10) Patent No.: US 7,798,980 B2
(45) Date of Patent: Sep. 21, 2010

(54) WIRE GUIDE HAVING DISTAL COUPLING TIP FOR ATTACHMENT TO A PREVIOUSLY INTRODUCED WIRE GUIDE

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/699,171

(22) Filed: Jan. 29, 2007

(65) Prior Publication Data
US 2007/0184707 A1 Aug. 9, 2007

Related U.S. Application Data

(60) Provisional application No. 60/763,523, filed on Jan. 31, 2006.

(51) Int. Cl.
*A61M 25/00* (2006.01)

(52) U.S. Cl. ..................................... 600/585

(58) Field of Classification Search .................. 600/585
See application file for complete search history.

(56) References Cited

U.S. PATENT DOCUMENTS

| | | | |
|---|---|---|---|
| 2,657,691 | A | 11/1953 | Nordstrom, Jr. |
| 3,521,620 | A | 7/1970 | Cook |
| 3,547,103 | A | 12/1970 | Cook |
| 3,656,680 | A | 4/1972 | Nomura |
| 3,739,784 | A | 6/1973 | Itoh |
| 3,890,997 | A | 6/1975 | Wilson |
| 4,548,206 | A | 10/1985 | Osborne |
| 4,569,347 | A | 2/1986 | Frisbie |
| 4,601,713 | A * | 7/1986 | Fuqua .................. 604/514 |
| 4,650,472 | A | 3/1987 | Bates |
| 4,665,906 | A | 5/1987 | Jervis |
| 4,824,435 | A | 4/1989 | Giesy et al. |
| 4,921,483 | A | 5/1990 | Wijay et al. |

(Continued)

FOREIGN PATENT DOCUMENTS

EP 0 436 303 A1 11/1990

(Continued)

OTHER PUBLICATIONS

International Search Report & Written Opinion (Jan. 3, 2008).

(Continued)

*Primary Examiner*—Max Hindenburg
*Assistant Examiner*—Michael C Stout
(74) *Attorney, Agent, or Firm*—Brink Hofer Gilson & Lione

(57) ABSTRACT

A coupling wire guide structured to be slidably coupled to a previously introduced wire guide. The coupling wire guide generally includes a main body having a distal end and a coupling tip connection to the distal end. The coupling tip includes a coupling portion defining a coupling passageway having a proximal port and a distal port. A slot is formed in the coupling tip and is in communication with the coupling passageway. The slot extends from the proximal port to the distal port, thereby permitting the coupling wire guide to be "clipped-on" to the mid-section of the previously introduced wire guide or any location having the most efficacy.

14 Claims, 4 Drawing Sheets

U.S. PATENT DOCUMENTS

| | | | |
|---|---|---|---|
| 4,925,445 A | 5/1990 | Sakamoto et al. | |
| 4,934,380 A | 6/1990 | De Toledo | |
| 4,984,581 A | 1/1991 | Stice | |
| 5,003,990 A | 4/1991 | Osypka | |
| 5,046,497 A | 9/1991 | Millar | |
| 5,069,226 A | 12/1991 | Yamauchi et al. | |
| 5,105,818 A | 4/1992 | Christian et al. | |
| 5,129,890 A | 7/1992 | Bates et al. | |
| 5,131,407 A | 7/1992 | Ischinger et al. | |
| 5,159,861 A | 11/1992 | Anderson | |
| 5,213,111 A | 5/1993 | Cook et al. | |
| 5,234,003 A | 8/1993 | Hall | |
| 5,242,759 A | 9/1993 | Hall | |
| 5,243,996 A | 9/1993 | Hall | |
| 5,251,640 A | 10/1993 | Osborne | |
| 5,267,958 A | 12/1993 | Buchbinder et al. | |
| 5,306,261 A | 4/1994 | Alliger et al. | |
| 5,318,527 A | 6/1994 | Hyde et al. | |
| 5,325,746 A | 7/1994 | Anderson | |
| 5,328,472 A | 7/1994 | Steinke et al. | |
| 5,328,480 A | 7/1994 | Milker et al. | |
| 5,344,413 A | 9/1994 | Allman et al. | |
| 5,354,257 A | 10/1994 | Roubin et al. | |
| 5,383,853 A | 1/1995 | Jung et al. | |
| 5,402,799 A | 4/1995 | Colon et al. | |
| 5,449,362 A | 9/1995 | Chaisson et al. | |
| 5,456,680 A | 10/1995 | Taylor et al. | |
| 5,488,959 A | 2/1996 | Ales | |
| 5,597,378 A | 1/1997 | Jervis | |
| 5,667,521 A | 9/1997 | Keown | |
| 5,738,667 A * | 4/1998 | Solar | 604/523 |
| 5,762,070 A | 6/1998 | Nagamatsu | |
| 5,776,079 A | 7/1998 | Cope et al. | |
| 5,776,100 A | 7/1998 | Forman | |
| 5,797,857 A | 8/1998 | Obitsu | |
| 5,810,876 A | 9/1998 | Kelleher | |
| 5,827,225 A | 10/1998 | Ma Schwab | |
| 5,873,842 A | 2/1999 | Brennen et al. | |
| 5,882,333 A | 3/1999 | Schaer et al. | |
| 5,891,056 A | 4/1999 | Ramzipoor | |
| 5,893,868 A | 4/1999 | Hanson et al. | |
| 5,993,424 A | 11/1999 | Lorenzo et al. | |
| 5,997,526 A | 12/1999 | Giba et al. | |
| 6,007,517 A * | 12/1999 | Anderson | 604/103.04 |
| 6,139,510 A | 10/2000 | Palermo | |
| 6,217,567 B1 | 4/2001 | Zadno-Azizi et al. | |
| 6,221,066 B1 | 4/2001 | Ferrera et al. | |
| 6,248,092 B1 | 6/2001 | Miraki et al. | |
| 6,254,549 B1 | 7/2001 | Ramzipoor | |
| 6,254,550 B1 | 7/2001 | McNamara et al. | |
| 6,290,693 B1 | 9/2001 | Jung, Jr. et al. | |
| 6,306,141 B1 | 10/2001 | Jervis | |
| 6,309,404 B1 | 10/2001 | Krzyzanowski | |
| 6,348,041 B1 | 2/2002 | Klint | |
| 6,348,045 B1 | 2/2002 | Malonek et al. | |
| 6,383,146 B1 | 5/2002 | Klint | |
| 6,471,697 B1 | 10/2002 | Lesh | |
| 6,475,167 B1 | 11/2002 | Fleming et al. | |
| 6,500,130 B2 | 12/2002 | Kinsella et al. | |
| 6,502,606 B2 | 1/2003 | Klint | |
| 6,517,518 B2 | 2/2003 | Nash et al. | |
| 6,530,899 B1 | 3/2003 | Savage | |
| 6,569,151 B1 * | 5/2003 | Nash et al. | 604/533 |
| 6,596,963 B2 | 7/2003 | Kelly | |
| 6,605,049 B1 | 8/2003 | Richardson et al. | |
| 6,613,002 B1 | 9/2003 | Clark et al. | |
| 6,638,372 B1 | 10/2003 | Abrams et al. | |
| 6,682,608 B2 | 1/2004 | Abrams et al. | |
| 6,805,676 B2 | 10/2004 | Klint | |
| 6,872,192 B2 * | 3/2005 | Nash et al. | 604/164.02 |
| 7,074,197 B2 | 7/2006 | Reynolds et al. | |
| 7,076,285 B2 | 7/2006 | Windheuser et al. | |
| 7,229,431 B2 * | 6/2007 | Houser et al. | 604/103.04 |
| 7,527,606 B2 | 5/2009 | Oepen | |
| 2002/0058888 A1 | 5/2002 | Biagtain et al. | |
| 2002/0169457 A1 | 11/2002 | Quinn | |
| 2003/0028127 A1 | 2/2003 | Balzum et al. | |
| 2003/0120208 A1 * | 6/2003 | Houser et al. | 604/103.04 |
| 2004/0073108 A1 | 4/2004 | Saeed et al. | |
| 2004/0116957 A1 | 6/2004 | Nishide | |
| 2004/0199087 A1 | 10/2004 | Swain et al. | |
| 2004/0215208 A1 | 10/2004 | Foushee et al. | |
| 2005/0027212 A1 | 2/2005 | Segner et al. | |
| 2005/0143770 A1 | 6/2005 | Carter et al. | |
| 2005/0148902 A1 | 7/2005 | Minar et al. | |
| 2005/0197663 A1 | 9/2005 | Soma et al. | |
| 2005/0209533 A1 | 9/2005 | Lorenz | |
| 2005/0267442 A1 | 12/2005 | Von Oepen | |
| 2005/0283122 A1 * | 12/2005 | Nordgren | 604/247 |
| 2006/0020256 A1 * | 1/2006 | Bell et al. | 604/523 |
| 2006/0100544 A1 | 5/2006 | Ayala et al. | |
| 2006/0100545 A1 | 5/2006 | Ayala et al. | |
| 2007/0060908 A1 | 3/2007 | Webster et al. | |
| 2007/0167065 A1 | 7/2007 | Melsheimer et al. | |
| 2007/0185414 A1 | 8/2007 | Urbanski et al. | |
| 2007/0191790 A1 | 8/2007 | Eells et al. | |

FOREIGN PATENT DOCUMENTS

| | | |
|---|---|---|
| EP | 0829269 A1 | 3/1998 |
| EP | 1057500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02 094364 A2 | 11/2002 |
| WO | WO2004/033016 | 4/2004 |
| WO | WO 2004/049970 A2 | 6/2004 |
| WO | WO 2004/050161 A1 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A1 | 8/2007 |
| WO | WO 2007/089893 A1 | 8/2007 |

OTHER PUBLICATIONS

Notification of Transmittal of International Preliminary Report on Patentability (Jan. 10, 2008).

The Journal of Invasive Cardiology entitled "Use of a Second Buddy Wire During Percutaneous Coronary Interventions: A Simple Solution for Some Challenging Situations" dated Apr. 25, 2005, pp. 1-8.

Office Action Restriction dated Mar. 3, 2008 U.S. Appl. No. 11/507,805 issued in related application.

International Search Report/Written Opinion—PCT/US2006/040843 (Feb. 7, 2007).

International Preliminary Report on Patentability—PCT/US2007/002741 (Jun. 25, 2008).

International Search Report—PCT/US2006/040843 (Jan. 31, 2007).

International Search Report—PCT/US2007/002743 (Jun. 14, 2007).

International Search Report—PCT/US2007/002741 (Jul. 9, 2007).

International Preliminary Report on Patentability and Written Opinion (Jul. 24, 2008) PCT/US2007/001066.

Office Action dated Sep. 26, 2008 U.S. Appl. No. 11/706,548 issued in related application.

Office Action dated Oct. 7, 2008 U.S. Appl. No. 11/507,993 issued in related application.

Office Action dated Oct. 15, 2008 U.S. Appl. No. 11/699,174 issued in related application.

International Search Report—PCT/US2006/042184 (Mar. 1, 2007).

International Search Report—PCT/US2007/001066 (Jun. 18, 2007).
International Search Report—PCT/US2007/004827 (Oct. 26, 2007).
Office Action dated Nov. 15, 2007 issued in related U.S. Appl. No. 11/652,430.
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 20, 2008 U.S. Appl. No. 11/763,355 issued in co-pending application.
Office Action dated Nov. 21, 2008 U.S. Appl. No. 11/549,473 issued in a co-pending pplication.
Office Action dated Dec. 11, 2008 U.S. Appl. No. 11/652,430 issued in co-pending application.
Advisory Action dated Jan. 16, 2009 U.S. Appl. No. 11/507,805 issued in co-pending application.
Advisory Action dated Mar. 6, 2009 U.S. Appl. No. 11/652,430 issued in co-pending application.
Office Action dated Mar. 30, 2009 U.S. Appl. No. 11/699,174 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 14, 2009 U.S. Appl. No. 11/507,993 issued in coo-pending application.
Office Action dated Jun. 4, 2009 U.S. Appl. No. 11/549,473 issued in co-pending application.
Office Action dated Jun. 9, 2009 U.S. Appl. No. 11/763,355 issued in co-pending application.
Office Action dated Jun. 12, 2009 U.S. Appl. No. 11/699,174 issued in co-pending application.
Advisory Action dated Jun. 25, 2009 U.S. Appl. No. 11/549,481 issued in co-pending application.
Advisory Action dated Jun. 22, 2009 U.S. Appl. No. 11/706,548 issued in co-pending application.
Office Action dated Jun. 23, 2009 U.S. Appl. No. 11/652,430 issued in co-pending application.
Office Action dated Aug. 3, 2009 U.S. Appl. No. 11/699,174 issued in co-pending application.
Office Action dated Sep. 16, 2009 U.S. Appl. No. 11/549,481 issued in co-pending application.
Office Action dated Oct. 1, 2009 U.S. Appl. No. 11/763,355 issued in co-pending application.
Office Action dated Oct. 14, 2009 U.S. Appl. No. 11/507,805 issued in co-pending application.
Office Action dated Oct. 23, 2009 U.S. Appl. No. 11/706,548 issued in co-pending application.
Office Action dated Dec. 9, 2009 U.S. Appl. No. 11/652,430 issued in co-pending application.
Office Action dated Dec. 14, 2009 U.S. Appl. No. 11/507,993 issued in co-pending application.
Office Action dated Mar. 12, 2010 U.S. Appl. No. 11/699,174 issued in co-pending application.
Office Action dated Apr. 2, 2010 U.S. Appl. No. 11/507,805 issued in co-pending application.
Office Action dated Apr. 6, 2010 U.S. Appl. No. 11/763,355 issued in co-pending application.
Office Action dated Apr. 21, 2010 U.S. Appl. No. 11/706,548 issued in co-pending application.
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 16, 2008 U.S. Appl. No. 11/763,355 issued in related application.
Office Action dated May 30, 2008 U.S. Appl. No. 11/507,805 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).

* cited by examiner

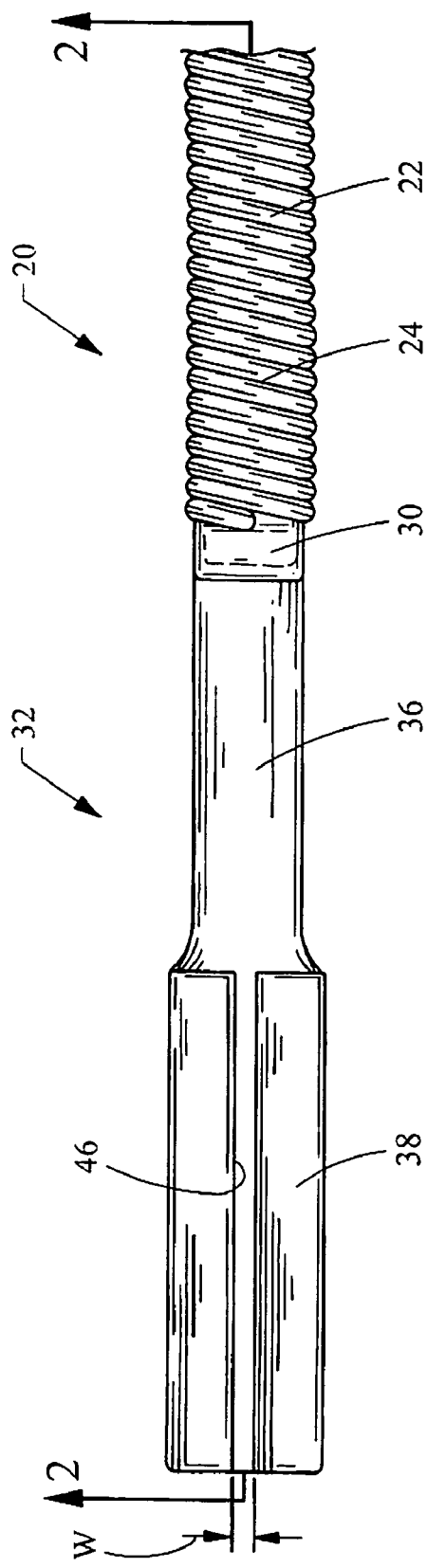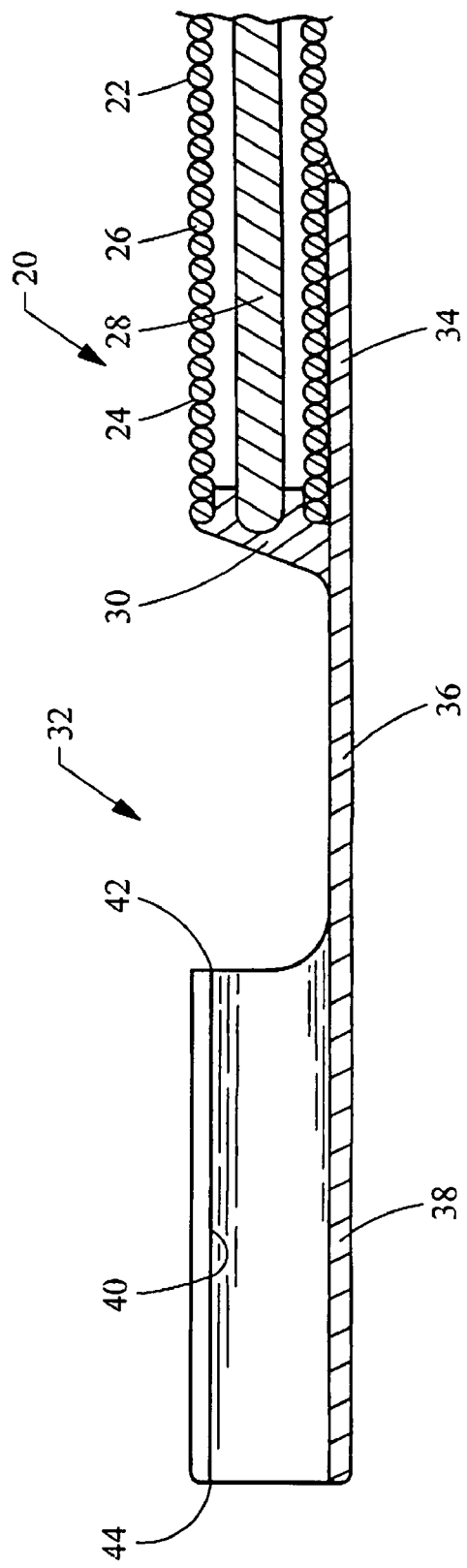

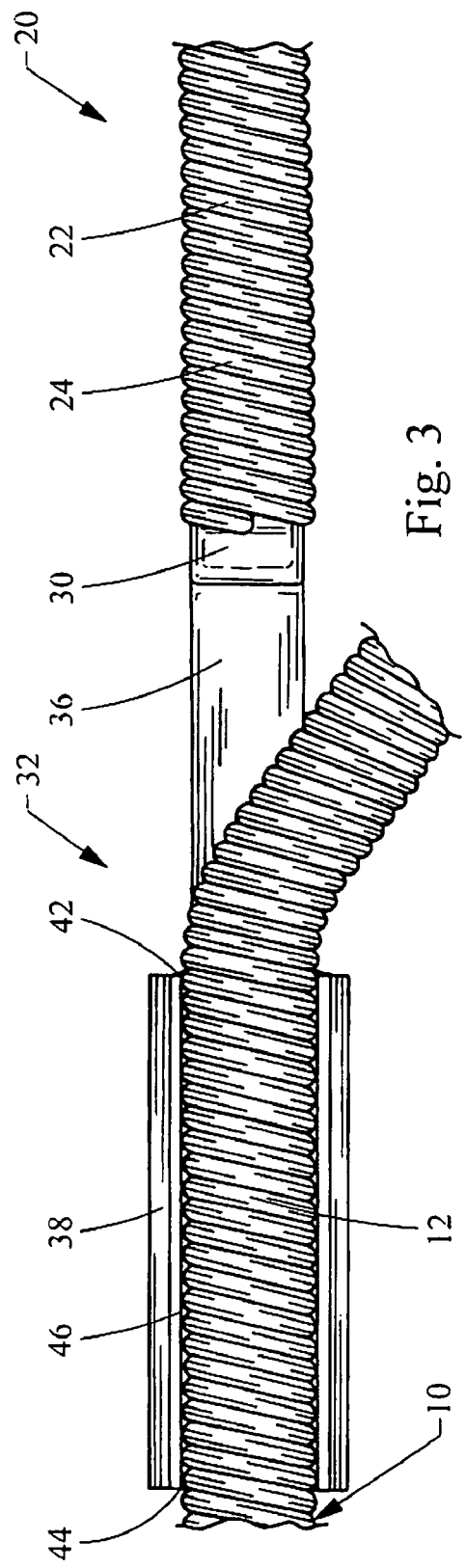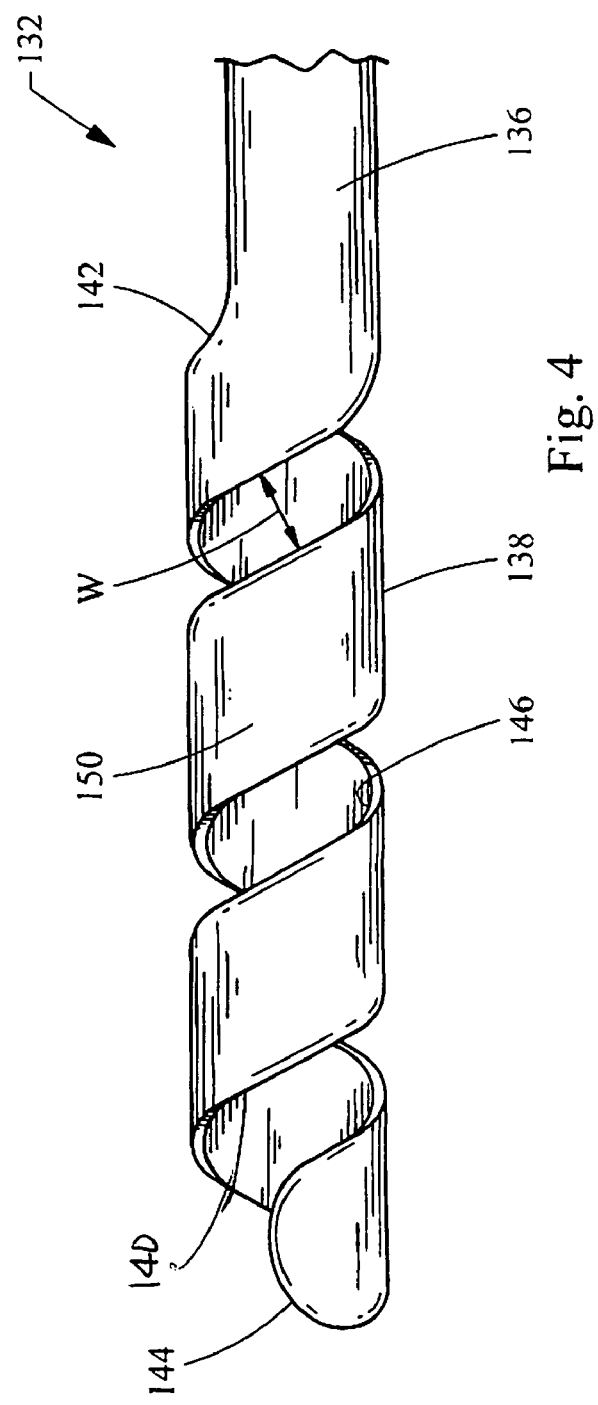

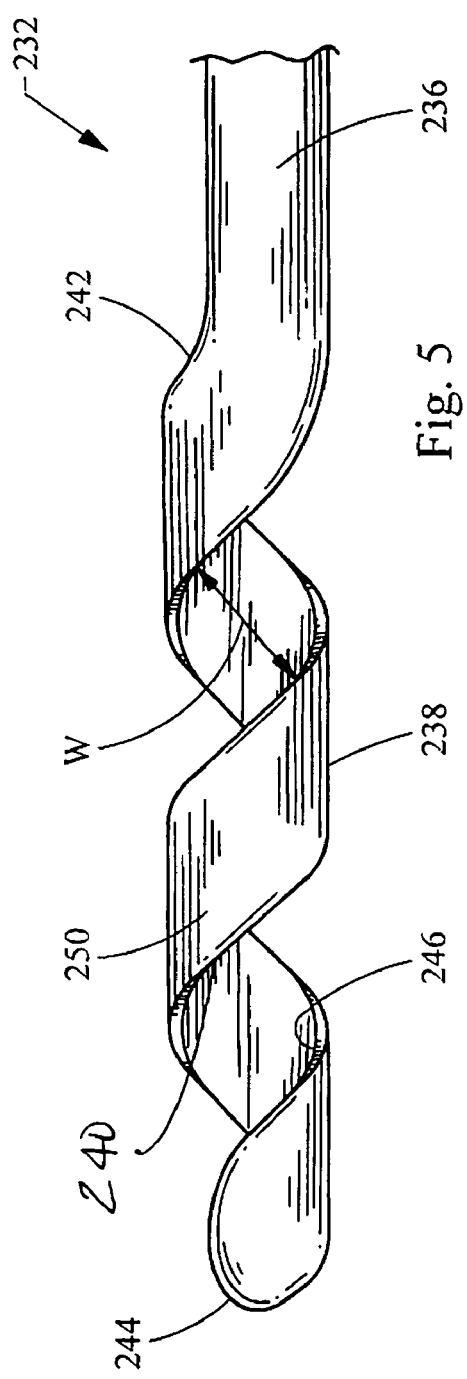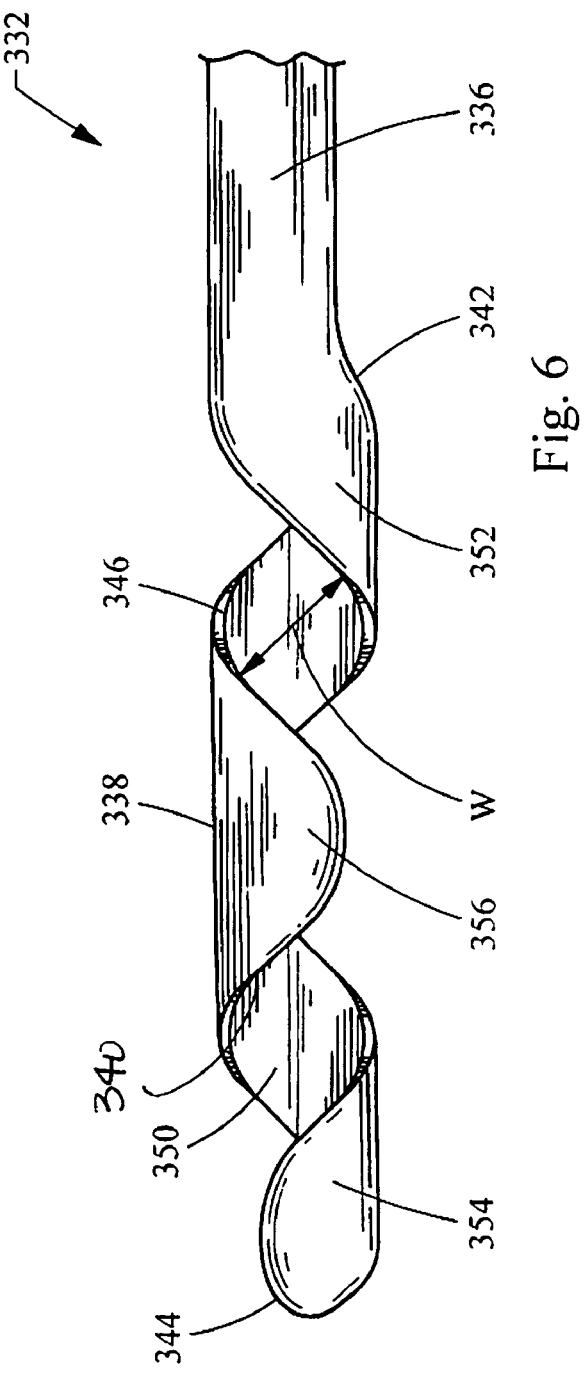

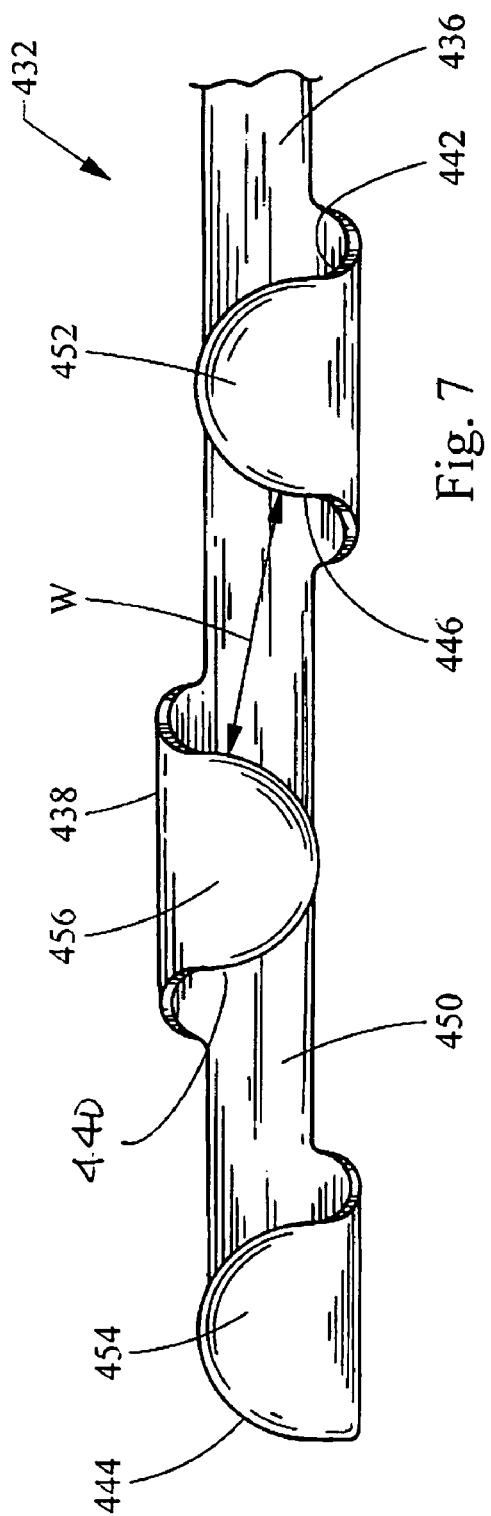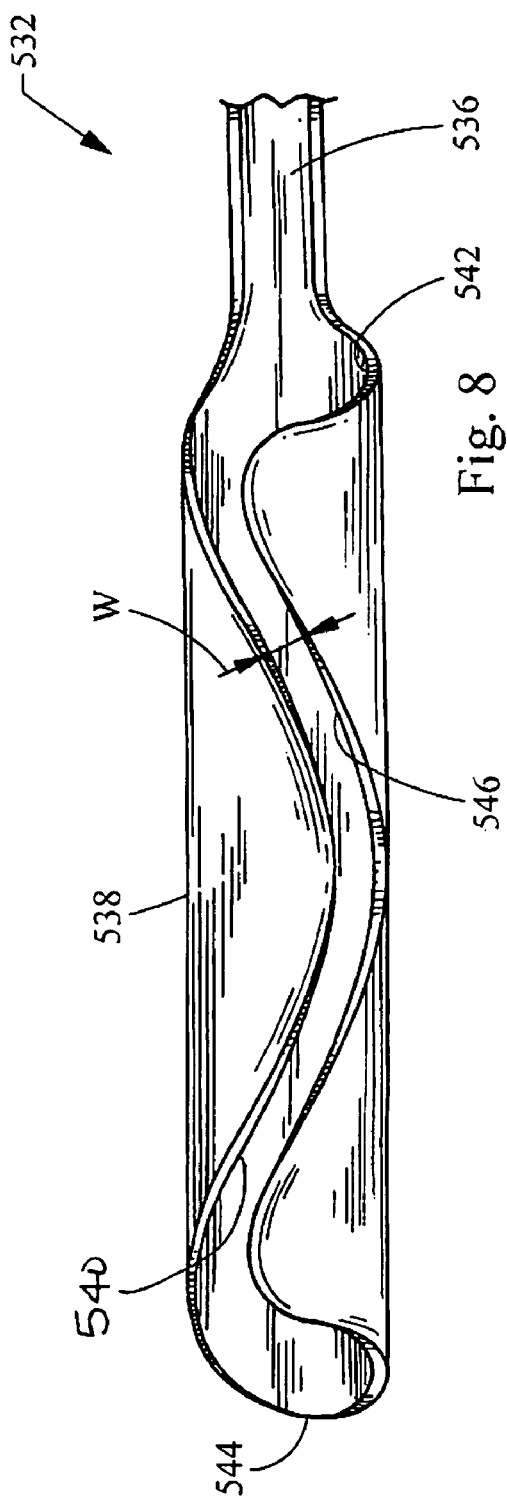

WIRE GUIDE HAVING DISTAL COUPLING TIP FOR ATTACHMENT TO A PREVIOUSLY INTRODUCED WIRE GUIDE

CROSS-REFERENCE TO RELATED APPLICATIONS

This application claims the benefit of U.S. Provisional Application Ser. No. 60/763,523 filed on Jan. 31, 2006, entitled "WIRE GUIDE HAVING DISTAL COUPLING TIP", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for intracorporeal procedures that may be easily and reliably traversed to a position proximate a previously introduced wire guide.

BRIEF SUMMARY OF THE INVENTION

The present invention provides a supporting wire guide for intracorporeal procedures that may be easily and reliably traversed to a position proximate a previously introduced wire guide. The supporting wire guide is a coupling wire guide that is structured to be slidably coupled to the previously introduced wire guide. In one embodiment constructed in accordance with the teachings of the present invention, the coupling wire guide generally includes a main body having a distal end and a coupling tip connected to the distal end. The coupling tip includes a coupling portion defining a coupling passageway having a proximal port and a distal port. A slot is formed in the coupling tip and is in communication with the coupling passageway. The slot extends from the proximal port to the distal port, thereby permitting the coupling wire guide to be "clipped-on" to the mid-section of the previously introduced wire guide or any location having the most efficacy.

According to more detailed aspects of the invention, the slot may take many forms. For example, the slot may follow a linear path, or the slot may follow a curved path. In several embodiments, the slot follows a helical path around the coupling portion. In several configurations, the slot has a width less than a diameter of the previously introduced wire guide, and in other configurations the slot has a width greater than or equal to the diameter of the previously introduced wire guide. In the later case, the coupling portion preferably includes retention tabs projecting into an area of the slot. The coupling portion is formed of a resilient material and thus the coupling portion flexes to adjust the size of the slot. Likewise, the coupling portion can adapt the contour of the coupling passageway to correspond to the contour of the previously introduced wire guide and the vasculature being traversed.

Another embodiment constructed in accordance with the teaching of the present invention provides a coupling wire guide having a main body and coupling tip. The coupling tip includes an attachment portion connection to the distal end of the main body. A coupling portion of the coupling tip defines a coupling passageway opening radially. The coupling portion further includes flexible retention tabs structured to hold the previously introduced wire guide within the coupling passageway. Preferably, the tabs project from opposing circumferential sides of the radially opening passageway and extend circumferentially around the coupling passageway. The retention tabs are preferably axially spaced apart and circumferentially overlap.

In yet another embodiment constructed in accordance with the teachings of the present invention, a coupling wire guide is provided having a main body and a coupling tip. The coupling tip is connected to a distal end of the main body. The coupling tip includes a coupling portion defining a coupling passageway and a laterally opening slot in communication with the coupling passageway. The coupling wire guide further includes means for directly attaching the coupling portion to the previously introduced wire guide at a point between the ends of the previously introduced wire guide and retaining the previously introduced wire guide within the coupling passageway during relative translation of the coupling wire guide and the previously introduced wire guide. The attachment means may include constructing the coupling portion of a resilient material and sizing the slot to have a width less than a diameter of the previously introduced wire guide. The attachment means may alternatively include forming the coupling portion as a helically wound strip. The attachment means may also alternately include retention tabs extending into the area of the slot.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a side view of a coupling wire guide constructed in accordance with the teachings of the present invention;

FIG. 2 is a cross-sectional view of the coupling wire guide depicted in FIG. 1;

FIG. 3 is a side view of the coupling wire guide shown in FIG. 1 opening to receive a previously introduced wire guide;

FIG. 4 is a side view of another embodiment of a coupling wire guide depicted in FIG. 1 in accordance with the teachings of the present invention;

FIG. 5 is a side view of another embodiment of a coupling wire guide depicted in FIG. 1 in accordance with the teachings of the present invention;

FIG. 6 is a side view of another embodiment of a coupling wire guide depicted in FIG. 1 in accordance with the teachings of the present invention;

FIG. 7 is a side view of another embodiment of a coupling wire guide depicted in FIG. 1 in accordance with the teachings of the present invention; and FIG. 8 is a side view of another embodiment of a coupling wire guide depicted in FIG. 1 in accordance with the teachings of the present invention.

DETAILED DESCRIPTION OF THE INVENTION

Turning now to the figures, FIGS. 1 to 3 depict a coupling wire guide 20 constructed in accordance with the teachings of the present invention. The coupling wire guide 20 is easily and reliably coupled to and traversed along a previously introduced wire guide 10 (FIG. 3), and notably is "side-loading" meaning the wire guide 20 may be attached by "clipping on" to a mid-section of the previously introduced wire guide 10. As used herein, the term "mid-section" refers to any point between the free ends of the previously introduced wire guide 10. In this manner, the coupling wire guide 20 may be coupled to and traversed along the previously introduced wire guide 10 without gaining access to the proximal end (or distal end) of the previously introduced guide wire 10, thereby saving time and increasing the versatility of the coupling wire guide 20.

As best seen in FIGS. 1 and 2, the coupling wire guide 20 generally includes a main body 22 and a coupling tip 32. The coupling tip 32 includes an attachment portion 34, a strip portion 36, and a coupling portion 38. The coupling portion 38 defines a coupling passageway 40 having a proximal port 42 and a distal port 44 through which the previously introduced wire guide 10 (FIG. 3) passes during the Buddy Wire or related techniques. While such techniques and wire guides are generally used in percutaneous interventional procedures, it will be recognized by those skilled in the art that the present invention may also be employed non-percutaneously, such as in endoscopic or other intracorporeal procedures.

As best seen in FIG. 2, the main body 22 generally comprises a coiled wire 26 disposed over a mandrel 28, a structure well known in the art. The attachment portion 34 of the coupling tip 32 is connected to a distal end 24 of the main body 22. An end cap 30 forms the distal tip of the main body 22, and is connected to the mandrel 28 through soldering or welding. The end cap 30 is also structured to guide the previously introduced wire guide 10 relative to the coupling tip 32. It will be recognized that the main body 22 of the coupling wire guide 20, as well as the previously introduced wire guide 10, may take numerous forms as many types of wire guides are known in the art, including solid wires, tubular wires, coiled wires and combinations thereof. For example, U.S. Pat. No. 5,243,996 discloses an exemplary solid wire mandrel having a coiled tip section, the disclosure of which is hereby incorporated by reference in its entirety.

To provide the side-loading function, the coupling portion 38 includes a slot 46 extending from the proximal port 42 to the distal port 44. By way of the slot 46, the coupling passageway 40 can be considered as opening laterally (i.e. radially), while the proximal and distal ports 42, 46 face axially. In this embodiment, the slot 46 follows a linear path generally parallel to an axis of the coupling passageway 40. Further, the slot 46 has a width W (as measured generally perpendicular to a central axis of the slot 46) that in its natural condition (as depicted in FIG. 1) is less than a diameter of the previously introduced wire guide 10. However, as shown in FIG. 3, the coupling portion 38 is formed of a resilient but flexible material such that the width W of the slot 46 may be increased to permit the previously introduced wire guide 10 to pass therethrough and into the coupling passageway 40. Once the previously introduced wire guide 10 is positioned within the passageway 40, the coupling portion 38 and its slot 46 return to their natural state as depicted in FIG. 1. Accordingly, the coupling portion 38, and preferably the entire coupling tip 32, is constructed of a resilient material such as nitinol (nickel-titanium superelastic alloy) or stainless steel, although any biocompatible resilient material may be employed including thermoplastics such PTFE, and other metals or alloys. It will also be recognized that the structure of the coupling portion, formed of a resilient material, permits the coupling tip 32 to adapt its contour to correspond to the contour of the previously introduced wire guide, and particularly the vasculature being navigated.

The attachment portion 34 is preferably constructed as a semi-annular strip (i.e. semi-annular in cross-section) which is connected to the distal end 24 of the main body 22. In particular, the attachment portion 34 is preferably soldered or welded to the main body 22. However, as the main body 22 and the coupling tip 32 may be constructed of numerous types of materials, it will be recognized that numerous types of attachment structures or methods may be employed such as adhesives, fasteners, material deformation, latches, plastic welding techniques and the like. The strip portion 36 is also preferably a semi-annular strip of material representing an extension of the attachment portion 34. The strip portion 36 provides flexibility to the coupling tip 32, and in particular permits the coupling portion 38 to deflect to one side when the coupling wire guide 20 is attached to and traversed along a previously introduced wire guide 10. At the same time, the strip portion 36 preferably has sufficient rigidity to maintain an aligned configuration of the coupling wire guide 20 in its natural state, as depicted in FIGS. 1 and 2. As such, the coupling wire guide 20 is suitable for use as a conventional wire guide when not coupled to a previously introduced wire guide 10. Preferably, the coupling tip 32, and namely the attachment portion 34, strip portion 36 and coupling portion 38 are unitarily formed of a common material, such as by laser cutting a tubular cannula to the desired shape, although numerous methods of information will be readily recognized by those skilled in the art.

Turning now to FIG. 4, another embodiment of a coupling tip 132 has been depicted for use in forming a coupling wire guide in accordance with the teachings of the present invention. In this embodiment, the coupling tip 132 is generally formed by a strip portion 136 which at its proximal end extends linearly, and then at its distal end follows a helical curved path to form the coupling portion 138. That is, the coupling portion 138 is formed of a strip of material 150 which is wound in a helical configuration. The helical path of the strip 150 is axially spaced to define a slot 146 having a width W. Thus, the slot 146 also follows a helical path having a width less than the diameter of the previously introduced wire guide. Further, the helical path of the strip 150 defines an internal coupling passageway 140 having a proximal port 142 and a distal port 144 sized to receive a previously introduced wire guide. As with the prior embodiment, the coupling tip 132, and especially the coupling portion 138, is formed of a resilient material which flexes such that the width W of the slot 146 may be adjusted. That is, the previously introduced wire guide 10 may be pressed through the slot 146. The previously introduced wire guide 10 may thus be sequentially passed through the slot 146 around its helical path. Alternatively, the helical strip 150 may be at least partially unwound, and then rewound around the previously introduced wire guide 10 in order to engage the previously introduced wire 10 at any point along its length.

FIG. 5 depicts yet another embodiment of a coupling tip 232 for forming a coupling wire guide in accordance with the teachings of the present invention. As with the embodiment depicted in FIG. 4, the coupling tip 232 includes a strip portion 236 which transitions into a coupling portion 238 formed by a strip of material 250 having a helical configuration. The helical strip 250 thus defines an internal coupling passageway 240 having proximal port 242 and distal port 244 sized to receive the previously introduced wire guide 10. The helical path is structured that the strip 250 leaves a slot 246 between adjacent turns of the helical strip 250, the slot 246 having a width W. Unlike the embodiment of FIG. 4, in this embodiment the slot 246 has a width W which greater than or equal to an outer diameter of the previously introduced wire guide 10. In this manner, the material forming the coupling tip 232 need not be as flexible (i.e. it may be more rigid) such that the previously introduced wire guide 10 may simply be positioned through the helical slot 246 and into the coupling passageway 240. However, a certain amount of flexibility is usually preferred for the navigation of tortuous pathways. It will also be recognized that in the embodiment of FIG. 4, the helical strip 150 includes about three revolutions, whereas in this embodiment the helical strip 250 follows about two revolutions, although any number of revolutions may be employed.

Turning now to FIG. 6, still yet another embodiment of a coupling tip 332 for use in forming a coupling wire guide in accordance with the teachings of the present invention has been depicted. The coupling tip 332 includes a strip portion 336 transitioning into a distal coupling portion 338. The coupling portion 338 is formed by a strip of material 350 which follows a helical path that changes direction at a mid-point of the coupling portion 338. Thus, the strip of material 350 forming the coupling portion 338 follows a curved path that defines a bi-directional helical slot 346 having a width W. Stated another way, the strip of material 350 forming the coupling portion 338 follows a curved path that defines three retention tabs 352, 354, 356 which project in opposing circumferential directions. The strip 350 defines a coupling passageway 340 having proximal and distal ports 342, 344 sized to receive a previously introduced wire guide 10. Accordingly, it will be recognized that this embodiment of the coupling tip 332 permits the attachment of the coupling tip at a mid-point of the previously introduced wire guide 10 with relatively little deformation of the previously introduced wire guide 10 while still providing secure interconnection thereto.

FIG. 7 depicts another embodiment of a coupling tip 432 for use in forming a coupling wire guide constructed in accordance with the teachings of the present invention. A strip portion 436 transitions into a coupling portion 438 formed by a strip 450 that is co-linear and aligned with the strip portion 436. That is, unlike the prior embodiments the strip 450 extends generally linearly to form the coupling portion 438. Similar to the prior embodiments, the material strip 450 has a semi-annular cross-sectional shape having a large slot 446. In this embodiment, a plurality of retention tabs 452, 454, 456 project into the area of the slot 446. The space between the tabs 452, 454, 456 define the width W of the slot 446. The tabs 452, 454, 456 have semi-annular configuration, which in combination with the material strip 450 defines the coupling passageway 440 having proximal and distal ports 442, 444 for receiving the previously introduced wire guide 10. The axial distance between the retention tabs 452, 454, 456 is preferably greater than or equal to a diameter of the previously introduced wire guide. The tabs 452, 454, 456 project from opposing circumferential sides of the slot 446, and are axially spaced apart and circumferentially overlap to securely retain the previously introduced wire guide 10 within the passageway 440 while providing easy access thereto via radially opening slot 446.

FIG. 8 depicts yet another embodiment of a coupling tip 532 for forming a coupling wire guide constructed in accordance with the teachings of the present invention. The coupling tip 532 includes a strip portion 536 which transitions into a coupling portion 538. Similar to the first embodiment depicted in FIGS. 1-3, the coupling portion 538 is formed by a generally tubular member defining an internal coupling passageway 540 having a proximal port 542 and distal port 544 for receiving a previously introduced wire guide 10. Likewise, the coupling portion 538 defines a slot 546 having a width W. However, in this embodiment the slot 546 follows a curved path between the proximal port 542 and distal port 544. In particular, the slot 546 follows a sinusoidal-like curvature, zig-zagging back and forth circumferentially along the length of the coupling portion 538. Accordingly, the coupling tip 532 provides extremely secure coupling between the coupling wire guide and a previously introduced wire guide, while also providing easy interconnection through "clippingon" the coupling portion 538 at any point along the length of a previously introduced wire guide 10.

Accordingly, it can be seen that all of the embodiments of the coupling wire guide include a coupling tip having means for directly attaching the coupling portion of the tip to the previously introduced wire guide at a point between the ends of the previously introduced wire guide. Likewise, each of the coupling tip retains the previously introduced wire guide within the coupling passageway during relative translation of the coupling wire guide and previously introduced wire guide. The coupling tips are connected to the distal end of a main body and include a coupling portion defining a coupling passageway and a laterally opening slot in communication with the coupling passageway. Generally, the attachment means may include constructing the coupling portion of a resilient material and sizing a slot extending from the proximal port to the distal port which is sized to have a width less than the diameter of the previously introduced wire guide. The attachment means may also include forming the coupling portion as a helically wound strip. The helical strip may have different axial spacing and thus differently sized helical slots, and may also change circumferential direction along its path. Further, the attachment means may include retention tabs extending into an area of the slot.

Through all of these various embodiments, interconnection of the coupling wire guide and a previously introduced wire guide is improved through interconnection at a midpoint of the previously introduced wire guide, while also providing a coupling tip which is generally aligned with the main body when decoupled and sufficiently resilient to be used alone, while also having the flexibility to adapt to the contour of the previously introduced wire guide and the vasculature that is being traversed.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide during intracorporeal procedures, the coupling wire guide comprising:
   a main body having a distal end defining a longitudinal axis, the distal end including an endcap defining a closed distal end surface;
   a coupling tip connected to the distal end of the main body, the coupling tip including a coupling portion, an attachment portion and a strip portion, the attachment portion connected to the main body, the strip portion extending between the coupling portion and attachment portion to space the coupling portion away from the attachment portion, the coupling portion including a tubular member defining a coupling passageway having a proximal port and a distal port, the proximal port facing axially towards the endcap wherein a previously introduced wire guide positioned within the coupling passageway engages the closed distal end surface of the endcap and is deflected away from the longitudinal axis;
   the strip portion having a semi-annular cross-sectional shape that permits movement of the coupling portion in a first radial direction and resists movement of the coupling portion in a second radial direction opposite the first radial direction, the semi-annular cross-sectional shape of the strip portion having a curvature matching a curvature of the distal end of the main body; and
   a slot formed in the coupling tip, the slot in communication with the coupling passageway and extending from the proximal port to the distal port.

2. The coupling wire guide of claim 1, wherein the slot follows a straight linear path.

3. The coupling wire guide of claim 1, wherein the slot follows a curved path.

4. The coupling wire guide of claim 1, wherein the slot has a width less than a diameter of the previously introduced wire guide.

5. The coupling wire guide of claim 1, wherein the coupling tip is structured to be attached at a mid-section of the previously introduced wire guide.

6. The coupling wire guide of claim 1, wherein the coupling portion is formed of a resilient material and is structured to adapt the contour of the coupling passageway to correspond to the contour of the previously introduced wire guide.

7. The coupling wire guide of claim 1, wherein the coupling portion flexes to adjust the size of the slot.

8. The coupling wire guide of claim 1, wherein the strip portion extends longitudinally such that the proximal port is longitudinally spaced away from the attachment portion.

9. The coupling wire guide of claim 1, wherein the distal port is axially facing.

10. The coupling wire guide of claim 1, wherein the closed distal end surface is angled relative to the longitudinal axis less than 90 degrees.

11. The coupling wire guide of claim 1, wherein the closed distal end surface is a generally flat surface angled relative to the longitudinal axis.

12. The coupling wire guide of claim 1, wherein the coupling tip is connected to an outer surface of the distal end of the main body.

13. The coupling wire guide of claim 1, wherein the main body has an outer surface formed by a wire.

14. The coupling wire guide of claim 1, wherein the slot is located on a side of the coupling portion corresponding to the first radial direction.

* * * * *